United States Patent [19]

Frey

[11] Patent Number: 5,598,051

[45] Date of Patent: Jan. 28, 1997

[54] BILAYER ULTRASONIC TRANSDUCER HAVING REDUCED TOTAL ELECTRICAL IMPEDANCE

[75] Inventor: Gregg W. Frey, East Wenatchee, Wash.

[73] Assignee: General Electric Company, Milwaukee, Wis.

[21] Appl. No.: 343,065

[22] Filed: Nov. 21, 1994

[51] Int. Cl.⁶ .................................... H01L 41/08
[52] U.S. Cl. ................... 310/334; 310/327; 310/331; 310/366
[58] Field of Search ................... 310/326–328, 310/331, 334, 366

[56] References Cited

U.S. PATENT DOCUMENTS

| | | | |
|---|---|---|---|
| 3,396,286 | 8/1968 | Anderson et al. | 310/328 |
| 4,166,967 | 9/1979 | Benes et al. | 310/334 |
| 4,240,003 | 12/1980 | Larson, III | 310/326 |
| 4,277,711 | 7/1981 | Hanafy | 310/334 |
| 4,381,470 | 4/1983 | Leach et al. | 310/327 |
| 4,404,489 | 9/1983 | Larson et al. | 310/334 |
| 4,437,033 | 3/1984 | Diepers | 310/334 |
| 4,446,395 | 5/1984 | Hadjicostis | 310/327 |
| 4,503,861 | 3/1985 | Entrekin | 128/661 |
| 4,564,980 | 1/1986 | Diepers | 310/334 |
| 4,763,148 | 8/1988 | Tsukimoto et al. | 310/328 |
| 5,099,459 | 3/1992 | Smith | 310/334 |
| 5,329,496 | 7/1994 | Smith | 310/334 |
| 5,381,385 | 1/1995 | Greenstein | 310/334 |
| 5,457,352 | 10/1995 | Müllen et al. | 310/327 |
| 5,488,957 | 2/1996 | Frey et al. | 128/663.01 |

OTHER PUBLICATIONS

"Multiple Layer Transducers for Broadband Applications" by J. Hossack et al. Ultrasonics Symposium, IEEE, 1991.
Goldberg et al., "Multi-Layer PZT Transducer Arrays for Improved Sensitivity", IEEE Ultrasonics Symposium, (1992), pp. 551–554.

Primary Examiner—Thomas M. Dougherty
Attorney, Agent, or Firm—Dennis M. Flaherty; John H. Pilarski

[57] ABSTRACT

An ultrasonic transducer having reduced total electrical impedance is constructed by stacking a plurality of piezoelectric transducer element arrays on top of each other. For a given thickness, the electrical impedance of a multilayer stack of piezoelectric transducer element arrays is a function of the number of layers. If the number of layers equals two, then the electrical impedance of the total stack-up of layers is reduced by a factor of one-quarter relative to the electrical impedance of a single layer of equal thickness. This facilitates matching the overall transducer impedance to that of the connecting cable.

6 Claims, 2 Drawing Sheets

BILAYER ULTRASONIC TRANSDUCER HAVING REDUCED TOTAL ELECTRICAL IMPEDANCE

FIELD OF THE INVENTION

This invention generally relates to probes used in ultrasonic imaging of the human anatomy. In particular, the invention relates to techniques for reducing the mismatch of the electrical impedance of an ultrasonic transducer array and the electrical impedance of the cables which carry signals to and from the signal electrodes of that ultrasonic transducer array.

BACKGROUND OF THE INVENTION

A conventional ultrasonic probe comprises a transducer package which must be supported within the probe housing. As shown in FIG. 1, a conventional transducer package 2 comprises a linear array 4 of narrow transducer elements. Each transducer element is made of piezoelectric material. The piezoelectric material is typically lead zirconate titanate (PZT), polyvinylidene difluoride, or PZT ceramic/polymer composite.

The design and fabrication of individual transducer elements with desirable acoustic properties, e.g., high sensitivity, wide bandwidth, short impulse response, and wide field of view, is a well known art.

Typically, each transducer element has a metallic coating on opposing front and back faces to serve as electrodes. The metallic coating on the front face serves as the ground electrode. The ground electrodes of the transducer elements are all connected to a common ground. The metallic coating on the back face serves as the signal electrode. The signal electrodes of the transducer elements are connected to respective electrical conductors formed on a flexible printed circuit board (PCB) 6.

During operation, the signal and ground electrodes of the piezoelectric transducer elements are connected to an electrical source having an impedance $Z_s$. When a voltage waveform is developed across the electrodes, the material of the piezoelectric element contracts at a frequency corresponding to that of the half-wave resonance of the piezoelectric thickness, thereby emitting an ultrasonic wave into the media to which the piezoelectric element is coupled. Conversely, when an ultrasonic wave impinges on the material of the piezoelectric element, the latter produces a corresponding voltage across its terminals and the associated electrical load component of the electrical source.

In conventional applications, each transducer element produces a burst of ultrasonic energy when energized by a pulsed waveform produced by a transmitter (not shown). The pulses are transmitted to the transducer elements via the flexible PCB 6. This ultrasonic energy is transmitted by the probe into the tissue of the object under study. The ultrasonic energy reflected back to transducer element array 4 from the object under study is converted to an electrical signal by each receiving transducer element and applied separately to a receiver (not shown).

The transducer package 2 also comprises a mass of suitable acoustical damping material having high acoustic losses, e.g., silver epoxy, positioned at the back surface of the transducer element array 4. This backing layer 12 is coupled to the rear surface of the transducer elements to absorb ultrasonic waves that emerge from the back side of each element so that they will not be partially reflected and interfere with the ultrasonic waves propagating in the forward direction.

Typically, the front surface of each transducer element of array 4 is covered with a first acoustic impedance matching layer 8 shown in FIG. 1. The first matching layer 8 may consist of a glass material such as Pyrex® borosilicate glass. Typically, a second acoustic impedance matching layer is later bonded to the first acoustic impedance matching layer. The impedance matching layers transform the high acoustic impedance of the transducer elements to the low acoustic impedance of the human body and water, thereby improving the coupling with the medium in which the emitted ultrasonic waves will propagate.

The transducer element array, backing layer and first acoustic impedance matching layer are all bonded together in a stack-up arrangement, as seen in FIG. 1.. During assembly of the ultrasonic probe, the transducer stack-up must be held securely within the probe housing (not shown in FIG. 1). Typically, this is accomplished by securing the transducer stack-up within a four-sided array case 14, i.e., a "box" having four side walls but no top or bottom walls, as shown in FIG. 2. The array case is made of electrically conductive material and provides a common ground for connection with the ground electrodes of the transducer elements. Preferably the array case is made of graphite.

The transducer stack-up is inserted into a recess in the array case 14 until the bottom surface of the first acoustic impedance matching layer 8 is flush with the bottom edge of the array case. The transducer stack-up is conventionally bonded inside the array case using epoxy. Then a second acoustic impedance matching layer 10 is conventionally bonded to those flush bottom surfaces (see FIG. 2). Matching layer 10 may consist of a plastic material, such as Plexiglas® acrylic resin plastic.

During assembly of an ultrasonic probe incorporating the structure of FIG. 2, transducer package 2 must be secured within the probe housing (not shown). The interior volume of the probe housing surrounding the transducer package is filled with thermally conductive potting material, e.g., heat-conductive ceramic granules embedded in epoxy. The potting material stabilizes the construction and assists in dissipating heat, generated during pulsation of the transducer element array, away from the probe surface/transducer face toward the interior/rear of the probe.

In the transmission mode, the piezoelectric ceramic of the transducer elements alternately compresses and expands in response to electrical signals received from a pulser circuit (not shown) via coaxial cables (not shown) electrically connected to the flexible PCB 6. The resulting compression waves propagate in both the forward and rearward directions, with the rearward-propagating compression waves being damped by the backing layer 12.

In the receiving mode, the piezoelectric ceramic of the transducer elements alternately compresses and expands in response to compression waves reflected back to the probe by the object being ultrasonically examined. These waves are transduced into electrical signals which are carried to a receiver circuit (not shown) by the flexible PCB 6 and the coaxial cable connected thereto.

The coaxial cables typically have a resistance of 50 to 100 ohms. For ideal operating conditions, it is desirable that the transducer elements have an electrical resistance equal to that of the coaxial cable to which they are electrically coupled. However, conventional transducer elements typically have a resistance on the order of 200 ohms, i.e., a resistance greater than the optimal resistance by a factor of 2 to 4.

SUMMARY OF THE INVENTION

The present invention solves the problem of impedance mismatch between a piezoelectric transducer and an electrical cable by reducing the electrical impedance of the transducer. In accordance with the invention, this is accomplished by constructing a transducer having multiple piezoelectric transducer element arrays stacked on top of each other. In accordance with one preferred embodiment of the invention, the number of layers is two. However, more than two layers can be sandwiched together in applications where greater reductions in the electrical impedance of the ultrasonic transducer are needed.

The invention is based upon the recognition that, for a given thickness, the electrical impedance of a multilayer stack of piezoelectric transducer element arrays is a function of the number of layers. If the number of layers equals N, then the electrical impedance of the total stack-up of layers is reduced by a factor of $1/N^2$ relative to the electrical impedance of a single layer of equal thickness. Thus, for a bilayer structure the electrical impedance of the transducer can be reduced by a factor of 4. This facilitates matching the overall transducer impedance to that of the connecting cable.

DETAILED DESCRIPTION OF THE PREFERRED EMBODIMENTS

Figure 1:
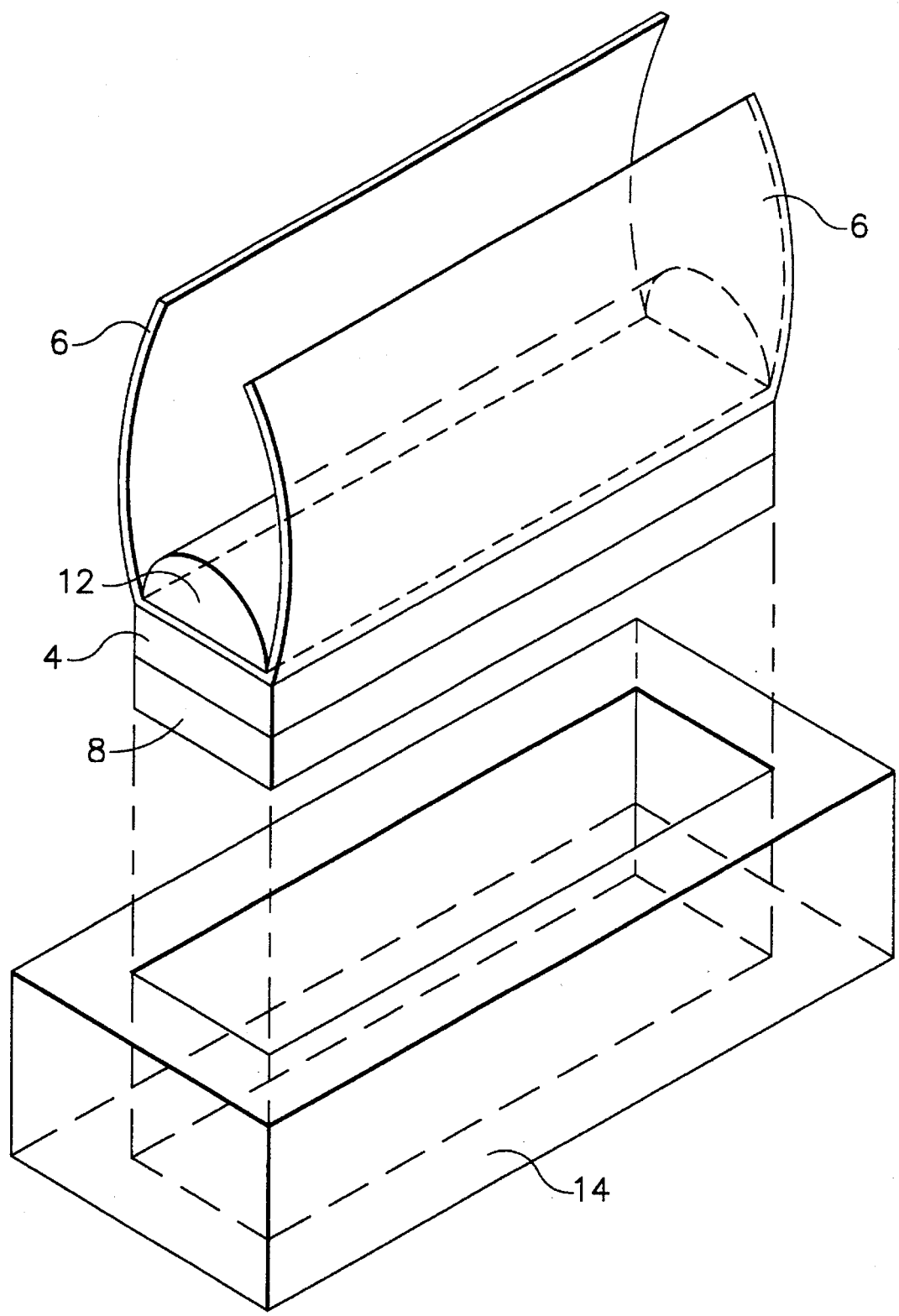
FIG. 1 is a schematic exploded view of parts of a conventional transducer package for use in an ultrasonic probe.
Figure 2:
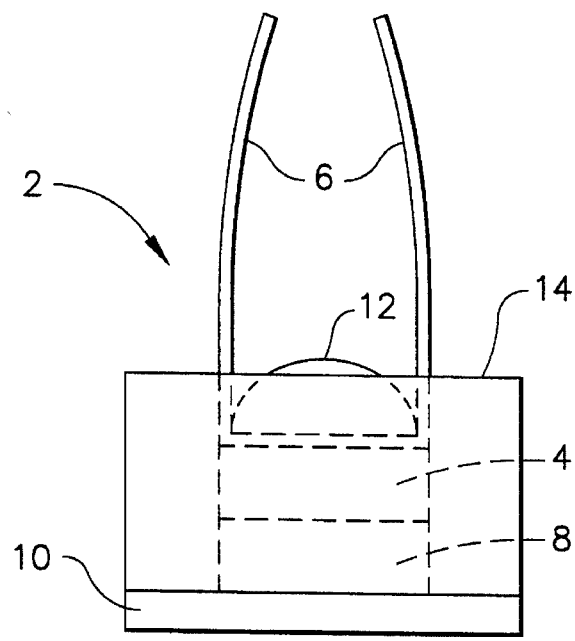
FIG. 2 is a schematic end view of a conventional transducer package showing the transducer stack-up installed inside the array case with an acoustic impedance matching layer bonded to the face of the assembly.
Figure 3:
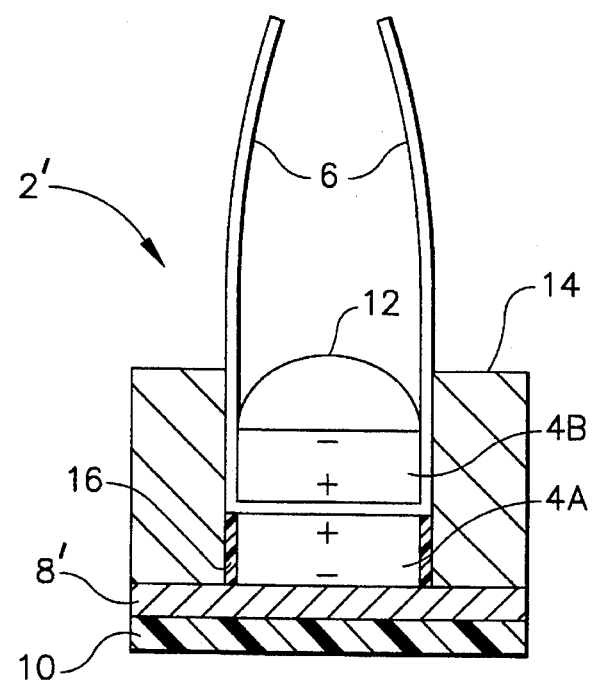
FIG. 3 is a schematic partly sectional view of a transducer stack-up having two stacked piezoelectric transducer element arrays in accordance with a preferred embodiment of the invention.

Referring to FIG. 3, a transducer package 2' in accordance with one preferred embodiment of the invention comprises a flexible PCB 6 sandwiched between a front transducer array 4A and a rear transducer array 4B. Each transducer array comprises a linear array of transducer elements made from piezoelectric ceramic. The number of transducer elements in each array is the same. The geometry and dimensions of the respective arrays are preferably identical.

Each transducer element has a signal electrode formed on one face and a ground electrode formed on the other face. In accordance with the present invention, the signal electrodes for front transducer array 4A are formed on its rear face and the ground electrodes for front transducer array 4A are formed on its front face. Conversely, the signal electrodes for rear transducer array 4B are formed on its front face and the ground electrodes for rear transducer array 4B are formed on its rear face. It is imperative that the front and rear transducer arrays be made of piezoelectric material which is poled in opposite directions, e.g., as indicated by the "+" and "−" symbols in FIG. 3. If the poling directions of the piezoelectric ceramic are as shown in FIG. 3, then the signal electrodes of the front and rear transducer arrays will oppose each other. On the other hand, if the poling directions of the piezoelectric ceramic are reversed, then the ground electrodes of the front and rear transducer arrays will oppose each other.

The piezoelectric ceramic elements of the transducer arrays 4A and 4B shown in FIG. 3 are driven in coincidence by electrical pulsing signals which both transducer arrays receive at their respective signal electrodes via conductive traces connected to a signal source. For example, the conductive traces may be formed on opposing sides of an insulative substrate of the flexible PCB 6 sandwiched between the stacked transducer arrays. Alternatively, it is possible to make conductive traces on one side of an insulating substrate, such as Kapton film; connect those traces to the signal electrodes on the rear face of front transducer array 4A; remove the Kapton substrate by etching to expose the other side of the conductive traces over an area corresponding in shape to the front face of rear transducer array 4B; and then connect the exposed traces to the signal electrodes on the front face of rear transducer array 4B.

In accordance with the present invention, a conventional backing layer 12 is bonded to the rear surface of the rear transducer array 4B. Backing layer 12 consists of a mass of acoustic damping material which damps out rearward propagating ultrasonic waves which exit the rear face of rear transducer array 4B.

The stack-up consisting of transducer arrays 4A and 4B and backing layer 12 is inserted inside the recess of a conventional rectangular array case 14. The stack-up is positioned so that the front face of front transducer array 4A is flush with the front endface of the array case. Then the stack-up is bonded in place using an epoxy 16. Array case 14 is preferably made of graphite or other suitable electrically conductive material. The electrically conductive array case is connected to ground.

In accordance with the preferred embodiment shown in FIG. 3, a rear acoustic impedance matching layer 8' is bonded to the front face of the transducer stack-up/array case combination. A suitable medium is interposed between the front face of front transducer array 4A and the rear face of acoustic impedance matching layer 8' to ensure acoustic coupling between these opposing surfaces. The material of the rear acoustic impedance matching layer 8' must have an acoustic impedance less than the acoustic impedance of the piezoelectric ceramic of front transducer array 4A. In addition, in accordance with the present invention, the material of rear acoustic impedance matching layer 8' is electrically conductive. The preferred material is copper-impregnated graphite. The electrically conductive material of rear acoustic impedance matching layer 8' is electrically connected to the array case 14 and to the ground electrodes on the front face of front transducer array 4A. In this way the ground electrodes of front transducer array 4A are connected to a common ground. The ground electrodes of rear transducer array 4B can also be connected to the array case 14, e.g., via conductive foil.

A front acoustic impedance matching layer 10 is bonded to the rear acoustic impedance matching layer 8'. The material of the front acoustic impedance matching layer 10 must have an acoustic impedance less than the acoustic impedance of the rear acoustic impedance matching layer 8'. A suitable medium is interposed between the front face of rear acoustic impedance matching layer 8' and the rear face of front acoustic impedance matching layer 10 to ensure adequate acoustic coupling therebetween.

To understand the operation of the bilayer transducer of the present invention, it is first necessary to understand the workings of a one-layer transducer. The basic principle of operation of a conventional one-layer transducer is that each piezoelectric element thereof radiates respective ultrasonic waves of identical shape but reverse polarity from its back surface and its front surface. A transducer is said to be half-wave resonant when the two waves constructively interfere at the front face, i.e., the thickness of the piezoelectric plate equals one-half of the ultrasonic wavelength. The half-wave frequency $f_0$ is the practical band center of most transducers. At frequencies lower than the half-wave resonance, the two waves interfere destructively so that there is progressively less acoustic response as the frequency approaches zero. Conversely, for frequencies above the half-wave resonance there are successive destructive interferences at $2f_0$ and every subsequent even multiple of $f_0$. Also, there are constructive interferences at every frequency which is an odd multiple of $f_0$.

The full dynamics of a multilayer transducer involve taking into account the impedances of each layer and the subsequent reflection and transmission coefficients. The dynamics of the transducer are tuned by adjusting the thicknesses and impedances of the layers. In the bilayer transducer, each transducer layer, in response to common pulsation, launches forward-propagating ultrasonic waves of opposite polarity from its front and back faces. For the purpose of this discussion, rearward-propagating ultrasonic waves will be ignored because they will be damped out by the backing layer 12. The forward-propagating ultrasonic wave launched from the rear face of forward transducer array 4A will destructively interfere with the forward-propagating ultrasonic wave launched from the front face of rear transducer array 4B. Therefore, the only surviving ultrasonic waves transmitted in the forward direction by the respective transducer arrays will be a forward-propagating ultrasonic wave launched from the rear face of rear transducer array 4B and a forward-propagating ultrasonic wave launched from the front face of forward transducer array 4A. Consistent with the dynamics for a single-layer transducer, the forward-propagating ultrasonic waves launched simultaneously from the rear face of rear transducer array 4B and from the front face of forward transducer array 4A will constructively interfere if they are separated by a distance equal to one-half of the ultrasonic wavelength. In other words, constructive interference will occur if the thickness of each transducer array is equal to one-quarter of the ultrasonic wavelength.

In order for the forward-propagating ultrasonic wave launched from the rear face of rear transducer array 4B to constructively interfere with the forward-propagating ultrasonic wave launched from the front face of front transducer array 4A, the conductive traces and electrodes sandwiched between the arrays must be acoustically transparent, i.e., ultrasound is transmitted through the layers of copper substantially unchanged. This can be achieved by forming copper conductive traces having a thickness less than 0.01 times the ultrasonic wavelength.

Using a two-layer piezoelectric transducer in place of a single-layer transducer of equal thickness reduces the total transducer element impedance by a factor of 4. For example, a single-layer piezoelectric transducer having an impedance of 200 ohms can be replaced with a two-layer piezoelectric transducer having one-quarter of the impedance, i.e, 50 ohms. This facilitates matching the overall transducer impedance to that of the connecting cable.

The foregoing preferred embodiment has been disclosed for the purpose of illustration. Variations and modifications which do not depart from the broad concept of the invention will be readily apparent to those skilled in the design of ultrasonic probes. For example, the number of transducer layers is not limited to two. The principle of the present invention can be extrapolated to multilayer transducers having three or more layers. For each variation, however, the total thickness of the multiple layers must equal one-half of the ultrasonic wavelength. Electrical connection means will be sandwiched between each pair of adjacent layers in a manner similar to that disclosed for the two-layer preferred embodiment. All such variations and modifications are intended to be encompassed by the claims set forth hereinafter.

I claim:

1. An ultrasonic transducer comprising:

an array case made of electrically conductive material electrically connected to ground and comprising four walls which define a rectangular recess, each of said four walls extending perpendicular to a reference plane;

a first planar transducer array of piezoelectric transducer elements arranged inside said recess of said array case at a first elevation and parallel to said reference plane, wherein each piezoelectric transducer element of said first planar transducer array has a front face with a first array front electrode on the surface thereof and a rear face with a first array rear electrode on the surface thereof;

a second planar transducer array of piezoelectric transducer elements arranged inside said recess of said array case at a second elevation less than said first elevation and parallel to said reference plane, wherein each piezoelectric transducer element of said second planar transducer array has a front face with a second array front electrode on the surface thereof and a rear face with a second array rear electrode on the surface thereof;

a multiplicity of electrically conductive traces sandwiched between said first and second planar transducer arrays, each conductive trace being electrically connected to a respective first array front electrode and to a respective second array rear electrode, wherein said first transducer array is poled in a first direction and said second transducer array is poled in a second direction opposite to said first direction, each of said first and second transducer arrays has a thickness equal to one-quarter of an ultrasonic wavelength transmitted by said transducer, and said conductive traces have a thickness less than 0.01 times said ultrasonic wavelength.

2. The ultrasonic transducer as defined in claim 1, further comprising an acoustic impedance matching layer acoustically coupled to said front faces of said second planar transducer array.

3. The ultrasonic transducer as defined in claim 1, further comprising an acoustic damping layer acoustically coupled to said rear faces of said first planar transducer array.

4. The ultrasonic transducer as defined in claim 1, wherein said multiplicity of conductive traces are incorporated in a flexible printed circuit board having a first portion sandwiched between said first and second planar transducer arrays and a second portion extending laterally beyond said transducer arrays, said flexible printed circuit board comprising a planar substrate made of electrically insulating material, said multiplicity of conductive traces being exposed on both sides of said first portion of said substrate.

5. The ultrasonic transducer as defined in claim 1, wherein said conductive traces are electrically connected to a signal source, and said first array rear electrodes and said second array front electrodes are electrically connected to said array case.

6. The ultrasonic transducer as defined in claim 1, wherein said conductive traces are electrically connected to said array case, and said first array rear electrodes and said second array front electrodes are electrically connected to a signal source.

* * * * *